US012053169B2

(12) United States Patent
Pic et al.

(10) Patent No.: US 12,053,169 B2
(45) Date of Patent: Aug. 6, 2024

(54) DEVICES AND METHODS FOR DELIVERING POWDERED AGENTS

(71) Applicant: Boston Scientific Scimed, Inc., Maple Grove, MN (US)

(72) Inventors: Andrew Pic, Northboro, MA (US); Daniel Congdon, Hudson, MA (US); Collin Murray, Maynard, MA (US); Matthew Robert Jagelski, Marlborough, MA (US); Joseph W. King, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 588 days.

(21) Appl. No.: 17/109,617

(22) Filed: Dec. 2, 2020

(65) Prior Publication Data
US 2021/0161515 A1   Jun. 3, 2021

Related U.S. Application Data

(60) Provisional application No. 62/942,898, filed on Dec. 3, 2019.

(51) Int. Cl.
*A61B 17/00* (2006.01)
(52) U.S. Cl.
CPC ............... *A61B 17/00491* (2013.01); *A61B 2017/00367* (2013.01); *A61B 2017/00495* (2013.01)

(58) Field of Classification Search
CPC .............. A61M 11/02; A61M 13/00; A61M 2039/2473; A61M 2039/2486;
(Continued)

(56) References Cited

U.S. PATENT DOCUMENTS 471,854 A   3/1892   Howard
881,238 A   3/1908   Hasbrouck
(Continued)

FOREIGN PATENT DOCUMENTS

CN   1901966 A   1/2007
CN   101401956 B   11/2012
(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Mohamed G Gabr
(74) *Attorney, Agent, or Firm* — Bookoff McAndrews, PLLC

(57) ABSTRACT

A device for delivering an agent may comprise a source of agent; a mixing chamber for receiving fluid and the agent; an outlet in fluid communication with the mixing chamber to deliver the fluid and the agent; and an actuator configured to (1) deliver a first flow of the fluid substantially free from the agent through the outlet; (2) after delivering the first flow, deliver a second flow of the fluid and the agent through the outlet; and (3) after delivering the second flow, deliver a third flow of the fluid substantially free from the agent through the outlet.

20 Claims, 10 Drawing Sheets

(58) Field of Classification Search
CPC .... A61M 2202/0007; A61M 2202/064; A61B 17/00491; A61B 2017/00495
See application file for complete search history.

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A * | 1/1980 | Barrington | A61C 3/025 604/24 |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A | 8/1995 | Terakura et al. | |
| 5,470,311 A | 11/1995 | Setterstrom et al. | |
| 5,884,621 A | 3/1999 | Matsugi et al. | |
| 5,951,531 A | 9/1999 | Ferdman et al. | |
| 6,003,512 A | 12/1999 | Gerde | |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0160897 A1* | 6/2010 | Ducharme | A61M 5/1409 604/82 |
| 2010/0305505 A1 | 12/2010 | Ducharme et al. | |
| 2011/0073200 A1 | 3/2011 | Overvaag et al. | |
| 2011/0121017 A1* | 5/2011 | Bergdahl | A47J 31/407 222/394 |
| 2011/0274726 A1 | 11/2011 | Guo et al. | |
| 2011/0308516 A1 | 12/2011 | Price et al. | |
| 2014/0228745 A1 | 8/2014 | Sharma et al. | |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1* | 10/2017 | Lee | B05B 7/1486 |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |

(56) References Cited

U.S. PATENT DOCUMENTS

| | | | |
|---|---|---|---|
| 2019/0232030 A1 | 8/2019 | Pic et al. | |
| 2021/0024187 A1 | 1/2021 | Fawcett et al. | |
| 2021/0069485 A1 | 3/2021 | Rogier | |

FOREIGN PATENT DOCUMENTS

| | | | |
|---|---|---|---|
| CN | 104010592 A | 8/2014 | |
| DE | 60215438 T2 | 8/2007 | |
| EP | 3052168 B1 | 11/2019 | |
| JP | H07118305 A | 5/1995 | |
| WO | 03013552 A1 | 2/2003 | |
| WO | 2004066806 A2 | 8/2004 | |
| WO | 2005062896 A2 | 7/2005 | |
| WO | 2006071649 A2 | 7/2006 | |
| WO | 2006088912 A2 | 8/2006 | |
| WO | 2008033462 A2 | 3/2008 | |
| WO | 2009061409 A1 | 5/2009 | |
| WO | 2015050814 A1 | 4/2015 | |
| WO | 2018157772 A1 | 9/2018 | |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion issued on Mar. 19, 2019 in counterpart International patent Application No. PCT/US2020/062836 (11 pages, in English).

* cited by examiner

DEVICES AND METHODS FOR DELIVERING POWDERED AGENTS

CROSS-REFERENCE TO RELATED APPLICATION(S)

This application claims the benefit of priority to U.S. Provisional Patent Application No. 62/942,898, filed Dec. 3, 2019, the entirety of which is incorporated herein by reference.

TECHNICAL FIELD

Various aspects of the disclosure relate generally to devices and methods for delivering agents. More specifically, aspects of the disclosure relate to devices for delivery of powdered agents, such as hemostatic agents.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY

Each of the aspects disclosed herein may include one or more of the features described in connection with any of the other disclosed aspects.

In an example, a device for delivering an agent may comprise a source of agent; a mixing chamber for receiving fluid and the agent; an outlet in fluid communication with the mixing chamber to deliver the fluid and the agent; and an actuator configured to (1) deliver a first flow of the fluid substantially free from the agent through the outlet; (2) after delivering the first flow, deliver a second flow of the fluid and the agent through the outlet; and (3) after delivering the second flow, deliver a third flow of the fluid substantially free from the agent through the outlet.

Any of the devices disclosed herein may include any of the following features. The actuator may transition from a first configuration to a second configuration. In the first configuration, the source of agent may not be in fluid communication with the mixing chamber. In the second configuration, the source of agent may not be in fluid communication with the mixing chamber. The actuator may include a valve defining an opening. In the first configuration, the opening may not be in fluid communication with the source of agent. In the second configuration, the opening may not be in fluid communication with the source of agent. The valve may include a first portion and a second portion. A spring may connect the first portion to the second portion. The valve may be able to transition from the first configuration to the second configuration only when a flow of the fluid is flowing through the mixing chamber. The actuator may include a body pivotable via at least one of a piston or a wire. The actuator may include a first rigid member and a second rigid member. The first rigid member may be pivotably coupled to the second rigid member. The second rigid member may include a trigger. The actuator may include a rotatable member having at least one blade extending from the rotatable member. The actuator may further include a gear. The actuator may include a first actuator for controlling a flow of the agent from the source of agent and a second actuator for controlling a flow of the fluid. The first actuator and the second actuator may be configured to be independently activated. The first actuator may be activated only if the second actuator is activated. The actuator may include a spring and a button valve. The actuator may include a first portion; a second portion defining an opening; and a spring extending from the first portion to the second portion. In the first configuration and the third configuration, the opening may not be in fluid communication with the source of agent. In the second configuration, the opening may not be in fluid communication with the source of agent. The agent may include a powder. The actuator may define an opening. In the first configuration and the third configuration, the opening may not be in fluid communication with the source of agent. In the second configuration, the opening may be in fluid communication with the source of agent such that the powder can pass through the opening.

In another example, a device for delivering an agent may comprise: a source of fluid; a source of powderized agent; a mixing chamber for receiving the fluid and the powderized agent; and an actuator configured to transition from a first configuration to a second configuration. In the first configuration, the source of agent may not be in fluid communication with the mixing chamber and a first flow of fluid substantially free from agent is received in the mixing chamber. In the second configuration, the source of agent may be in fluid communication with the mixing chamber and the powderized agent and a second flow of fluid are received in the mixing chamber.

Any of the devices disclosed herein may have any of the following features. The actuator may be further configured to transition from the second configuration to the first configuration after transitioning form the first configuration to the second configuration.

In an example, a method of delivering an agent may comprise: activating an actuator to cause: delivering a first flow of fluid, wherein the fluid is substantially free from a agent; after delivering the first flow, delivering a second flow of the fluid combined with the agent; and after delivering the second flow, delivering a third flow of fluid, wherein the fluid is substantially free from a agent.

Any of the methods or devices disclosed herein may include any of the following features. The agent may include a hemostatic agent. The fluid may be a pressurized fluid. During the delivering of the first flow and the third flow, an opening of the actuator may not be in fluid communication with a source of the agent. During the delivering of the second flow, an opening of the actuator may be in fluid communication with the source of the agent.

It may be understood that both the foregoing general description and the following. It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects of the disclosure and together with the description, serve to explain the principles of the disclosure.

DETAILED DESCRIPTION

A dual-stage actuation mechanism may be used to deliver an agent (e.g., a powdered agent) from a delivery system to a site of a medical procedure. The actuation mechanism may function to, upon activation, first deliver a flow of fluid, without the agent, through the delivery system and to the site. Then, a combined flow of the fluid and the agent may be delivered. Following delivery of a desired amount of the agent, the fluid may again be delivered without the agent. Delivery of fluid alone, before and after delivery of the agent, may facilitate flushing of components of the delivery system and may prevent clogging of the delivery system.

Figure 1A:
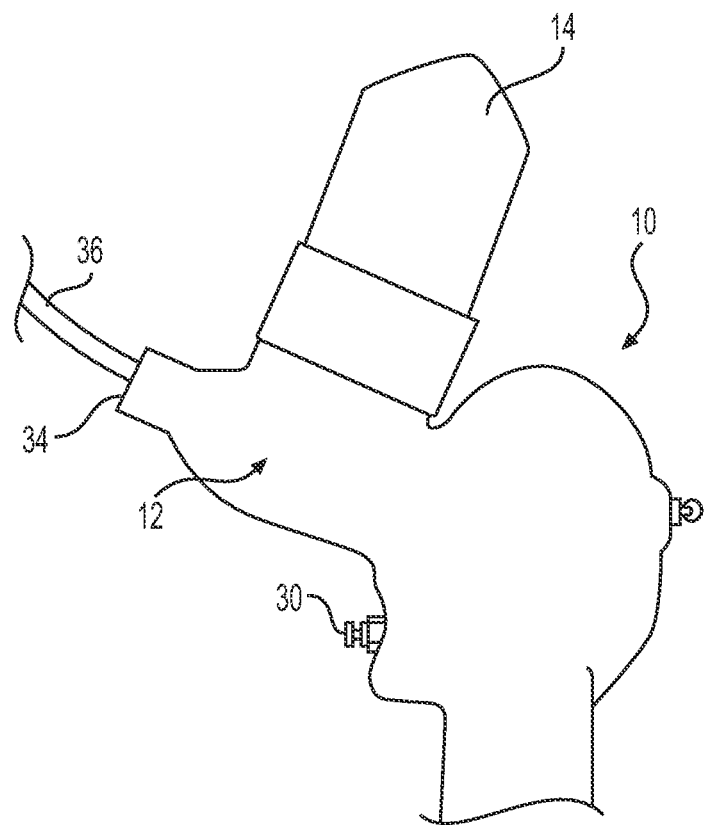
FIGS. 1A-1C show aspects of an exemplary delivery device.

FIG. 1A shows a delivery system 10, which may be a powder delivery system. Delivery system 10 may include a body 12. Body 12 may have a variety of features, to be discussed in further detail herein. The features described herein may be used alone or in combination and are not mutually exclusive. Like reference numbers and/or terminology are used to denote similar structures, when possible.

Figure 1B:
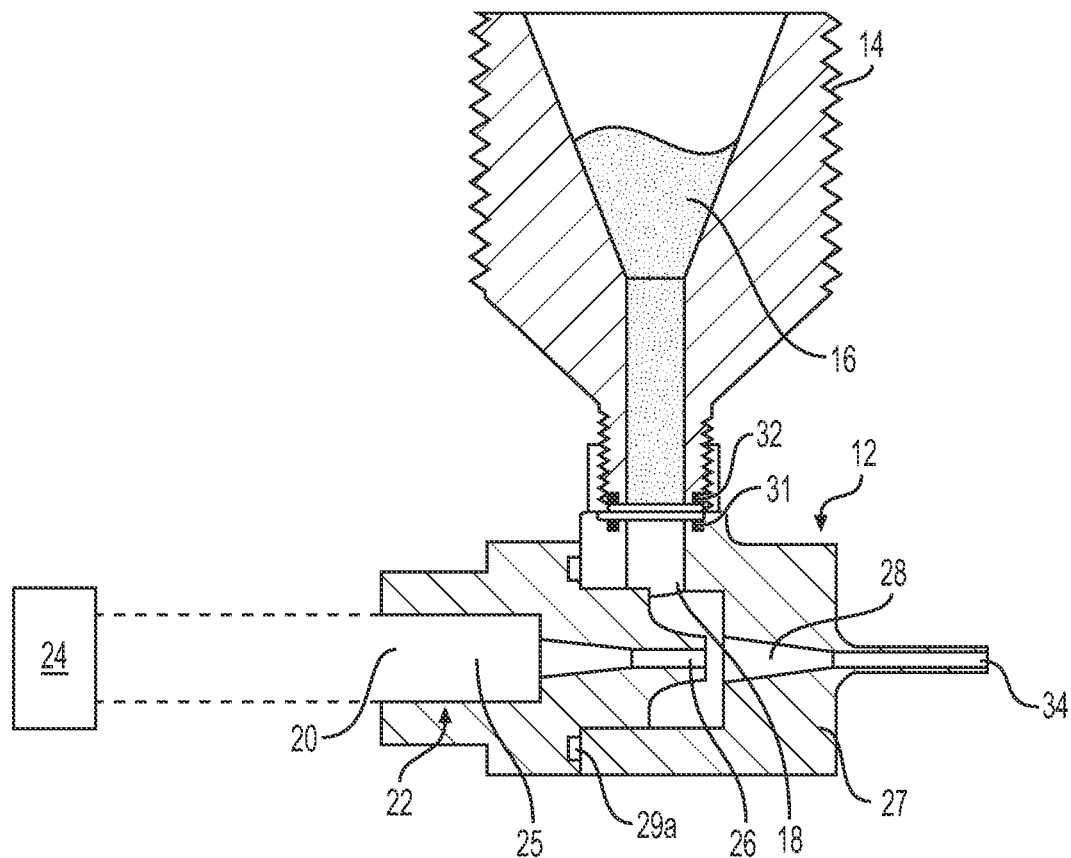

FIG. 1B shows a cross-section of an exemplary body 12, which may be a component of delivery system 10. Body 12 may include or may be configured to receive an enclosure 14 (or other source) storing an agent 16. Enclosure 14 may be screwed onto body 12 for providing agent 16 to body 12, or a lid/store of agent 16 may be screwed onto enclosure 14 for supplying agent 16 to enclosure 14. Agent 16 may be, for example, a powdered agent, such as a hemostatic agent. Agent 16 may alternatively be another type of agent or form of agent (e.g., a liquid or gel agent) and may have any desired function. Enclosure 14 may be removably attached to other components of delivery system 10, including components of body 12. Body 12 may have an agent inlet 18 in fluid communication with enclosure 14 for receiving agent 16 from enclosure 14. Body 12 may include a fluid inlet 20 for receiving fluid, such as pressurized fluid, from a source 24 (e.g., a disposable canister, a tank, a supply line, etc.).

Figure 1C:
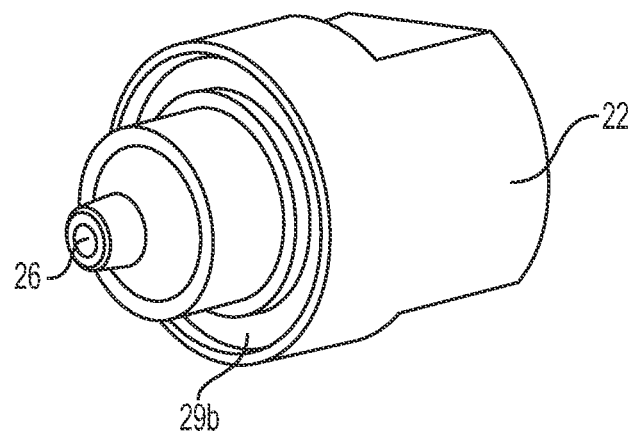

Body 12 may include a nozzle 22, shown separately in FIG. 1C. Nozzle 22 may include a nozzle chamber 25, which may be in fluid communication with source 24. Nozzle chamber 25 may terminate in an opening 26. A diameter of nozzle opening 26 may be between 0.015 and 0.030 inches (e.g., 0.020 inches). Opening 26 may be positioned approximately along a longitudinal axis of agent inlet 18. Opening 26 may be positioned behind, slightly behind, slightly in front of, or directly in front of agent inlet 18.

Opening 26 may be in fluid communication with a mixing body 27 defining a mixing chamber 28 for combining agent 16 with fluid from source 24. Nozzle 22 may connect with mixing body 27 of body 12 via any suitable fastening method (e.g., nuts, bolts, being formed of a continuous material with mixing body 27, etc.) An O-ring 29a may sit in an annular seat 29b of nozzle 22 so as to provide a seal between nozzle 22 and mixing body 27. Mixing body 27 may connect with enclosure 14 via any suitable fastening method (such as screwing onto mixing body 27, as shown) and may also include seals 31, 32 to provide seals between enclosure 14 and mixing body 27 or other portions of body 12.

A combination of agent 16 and fluid may be delivered from outlet 34 of body 12. Outlet 34 may be in fluid communication with a catheter 36 (see FIG. 1A) or other component for delivering the combination of agent 16 and fluid to a desired location within a body lumen of a patient. Mixing chamber 28 may be in fluid communication with outlet 34 and mixing chamber 28 and/or outlet 34 may be configured to allow for fluid connection with catheter 36. A diameter/width of outlet 34 may be the same as or approximately the same as a diameter/width of catheter 36 or an internal lumen of catheter 36. A lack of edges formed between mixing body 27 (including mixing chamber 28 and outlet 34) may reduce clogging of agent passing into catheter 36. A catheter may have an inner diameter of 0.080 inches, 0.050 inches, or 0.030 inches, for example, and mixing chamber 28, outlet 34, and or/mixing body 27 may be dimensioned for compatibility with those sizes of catheter.

Delivery system 10 may include an actuation mechanism 30 for controlling a release of agent 16 and/or fluid via outlet 34. For example, actuation mechanism 30 may include a trigger, button, slider, knob, lever, or other suitable mechanism. Actuation mechanism may cause agent 14 and/or fluid to enter mixing chamber 28, where agent 14 and fluid may be combined. As discussed below, delivery system 10 may include more than one actuation mechanism 30. For example, multiple actuation mechanisms 30 may be used to separately control a flow of fluid through fluid inlet 20 and a flow of agent from enclosure 14 through agent inlet 18.

Figure 2A:
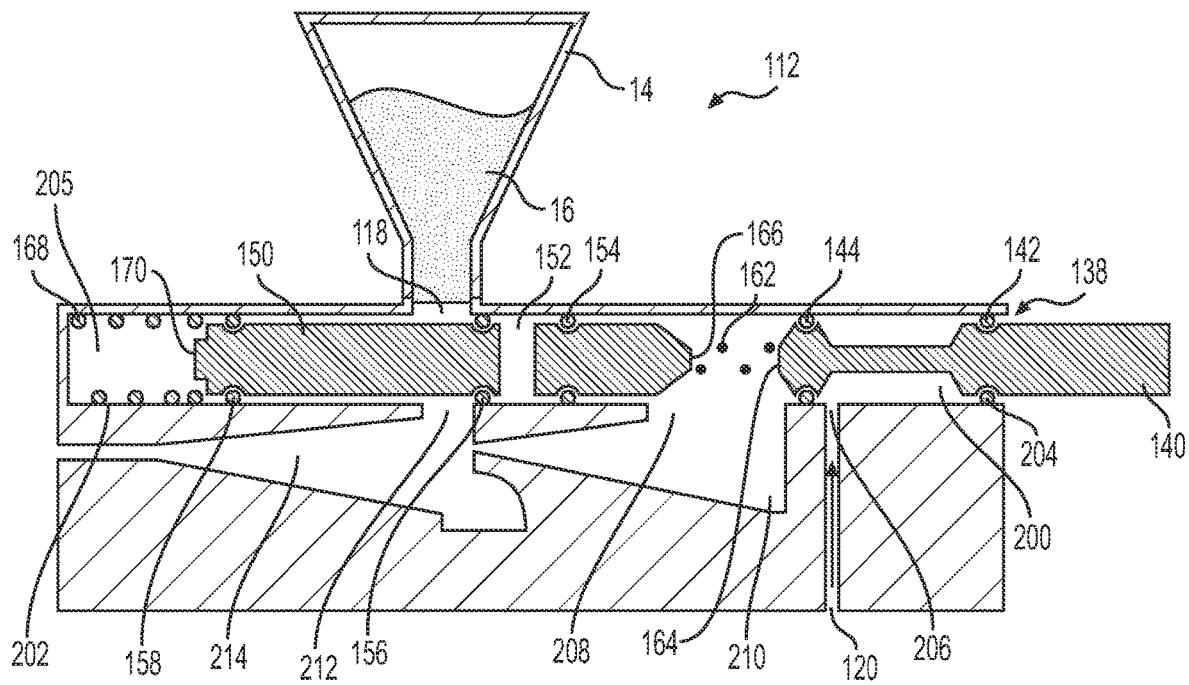
FIGS. 2A-7D show various example actuation mechanisms for use of a delivery device, including in the delivery device of FIGS. 1A-1C.
Figure 2B:
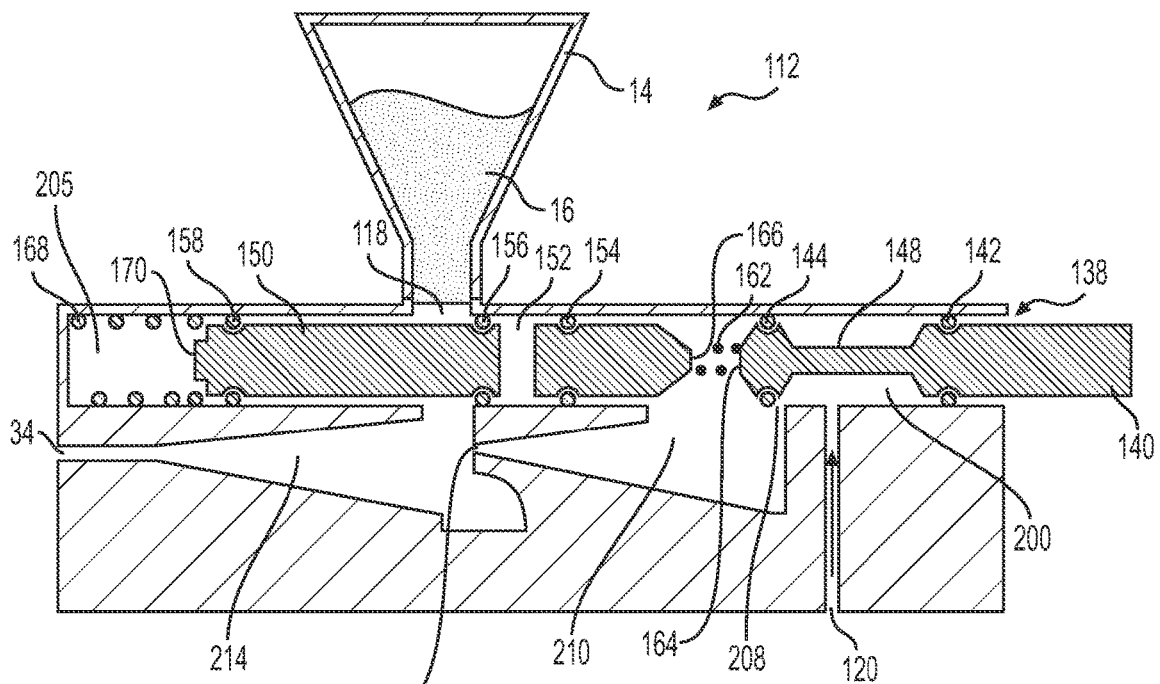
Figure 2C:
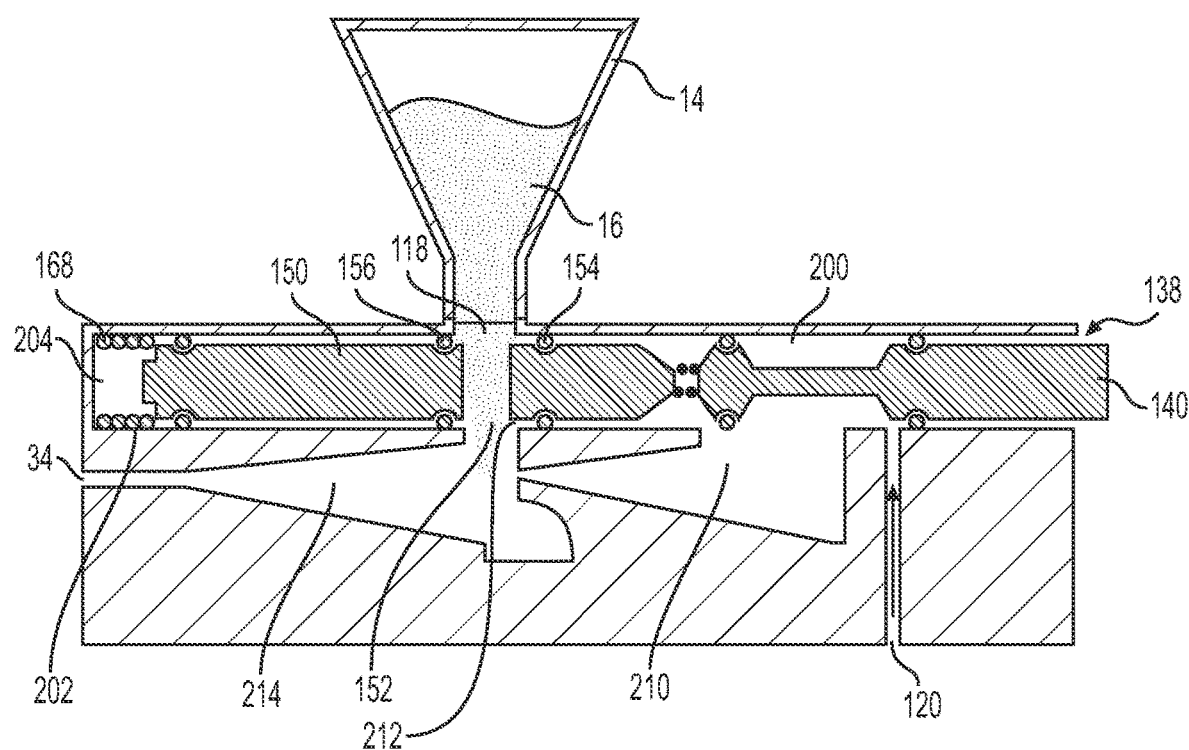

FIGS. 2A-2C show cross-sectional views of an exemplary body, which may be a component of delivery system 10. Body 112 may include an agent inlet 118, which may be in fluid communication with enclosure 14 storing an agent 16. Agent inlet 118 may be appropriately sized so as to allow passage of agent 16 therethrough. Agent inlet 118 may have approximately the same size as opening 152, described below. Agent inlet 118 may be an opening formed in body 112. Agent inlet 118 may be a portion of enclosure 14, particularly where enclosure 14 is not detachable from body 112. Alternatively, enclosure 14 may include an opening formed therein, which may be in fluid communication with agent inlet 118. Body 112 also may include a fluid inlet 120 for receiving fluid from source 24 (see FIG. 1C). The arrow in FIG. 2B shows the direction of fluid flow into inlet 120. Body 112 may also include a valve 138 for controlling flow of fluid through fluid inlet 120 and agent 16 through agent inlet 118. Valve 138 may be operatively connected to actuation mechanism 30 (see FIG. 1A).

Valve 138 may include a first portion 140. First portion 140 may have a first seal 142 and a second seal 144 received thereon. First seal 142 and/or second seal 144 may be, for example, O-ring seals. First portion 140 may also include a neck portion 148, between first seal 142 and second seal 144. Neck portion 148 may have a smaller cross-sectional diameter than other portions of first portion 140 (e.g., those receiving first seal 144 and second seal 146).

Valve 138 may also include a second portion 150. Second portion 150 may define an opening 152. Opening 152 may extend through an entire thickness of second portion 150 in a direction parallel to longitudinal axis of agent inlet 118 (but not through an entire width of second portion 150). Second portion 150 may have a third seal 154, fourth seal 156, and fifth seal 158 received thereupon. Third seal 154 may be on a first side of opening 152, more proximate to first portion 140. Fourth seal 156 may be on a second, opposite side of opening 152. Fifth seal 158 also may be on the second side of opening 152. First portion 140 may be closer to fourth seal 156 than to fifth seal 158.

A first spring 162 may extend between and connect first portion 140 and second portion 150. First spring 162 may be fixedly connected to an end 164 of first portion 140 and to an end 166 of second portion 150. First portion 140 may taper to first end 164, which may have a smaller cross-sectional diameter than other portions of first portion 140. Second portion 150 may taper to first end 166, which may have a smaller cross-sectional diameter than other portions of second portion 150. First end 166 may be an end of second portion 150 that is closest to third seal 154. A second spring 168 may extend from a second end 170 of second portion 150. Second end 170 may be an end of second portion 150 that is closest to fifth seal 158. First spring 162 may have a smaller spring constant than second spring 168 (i.e., first spring 162 may be a weaker spring than second spring 168). An equivalent force on first spring 162 and second spring 168 may cause first spring 162 to compress more than second spring 168.

Valve 138 may be received within a cavity 200 of body 112. Cavity 200 may be defined by surface(s) 202. First cavity 200 may have a first opening 204, which is at one end of cavity 200. Cavity 200 may have a second opening 206, which is in fluid communication with fluid inlet 120 and source 24. A third opening 208 of cavity 200 may be in fluid communication with a fluid nozzle chamber 210. A fourth opening 212 of cavity 200 may be in fluid communication with a mixing chamber 214, which may have any of the features of mixing chamber 30. Fourth opening 212 may be aligned or approximately aligned with agent inlet 118 so as to be in selective fluid communication with agent inlet 118. Second spring 168 may contact surface 202 at an end 205 of cavity 200 that is opposite from the end of cavity 200 having first opening 204.

Seals 142, 144, 154, 156, 158 may have dimensions and measurements on a durometer such that they form seals with surface(s) 202 of cavity 200. Seals 142, 144, 154, 156, 158 may also permit sliding movement of valve 138 within cavity 200.

FIG. 2A shows body 112 in a first configuration, in which agent 16 is not permitted to flow into cavity 200 via agent inlet 118, and fluid is not permitted to flow into cavity 200 via fluid inlet 120. Fourth seal 156 and fifth seal 158 may be positioned on either side of agent inlet 118 so that agent 16 may not pass between seals 156, 158 and surface(s) 202, thus preventing flow of agent 16. First seal 142 and second seal 144 may be positioned on either side of fluid inlet 120. Seals 142, 144, may prevent movement of fluid from fluid inlet 120 between seals 142, 144 and surface(s) 202. In the first configuration, springs 162, 164 may be in relaxed, uncompressed states.

FIG. 2B shows body 112 in a second configuration, in which fluid is permitted to flow into cavity 200 via fluid inlet 120. In operation, when actuation mechanism 30 is activated, first portion 140 of valve 138 may translate within cavity 200, in a first direction toward end 205 of cavity 200. Actuation mechanism 30 may be a separate component, or a surface of valve 138 may serve as an actuation mechanism and may receive a force from a user's hand. First portion 140 may exert a force first against spring 162, causing first spring 162 to compress. Because first spring 162 is weaker than second spring 168 and/or because second portion 150 may not move until first spring 162 is compressed a selected amount, second portion 150 may not immediately move along with first portion 140.

As shown in FIG. 2B, in the second configuration, an entirety of second seal 144 may not be in contact with surface(s) 202. For example, second seal 144 may be aligned with a portion of third opening 208. Thus, fluid from fluid inlet 120 may pass between first portion 140 and surface(s) 202 (e.g., along neck portion 148). The fluid may then pass through third opening 208 into fluid nozzle chamber 210. The fluid may then pass through a fluid nozzle opening 220, into mixing chamber 214. The fluid may then exit through outlet 134.

In the second configuration of FIG. 2B, second portion 150 may remain in the same position or in approximately the same position as in the first configuration (FIG. 2A). Therefore, for the reasons discussed above, agent 16 may not be permitted to flow into cavity 200 via agent inlet 118. As a result, only the fluid from source 24 may exit outlet 134.

As actuation mechanism 30 continues to be activated, second portion 150 may begin to move in the first direction (to the left in the Figures), after first spring 162 has been sufficiently compressed, when the force is sufficient to compress second spring 168. Valve 138 may be thusly transitioned from the second configuration (FIG. 2B) to a third configuration of FIG. 2C. In the third configuration, third seal 154 and fourth seal 156 may be disposed on opposite sides of agent inlet 118, and opening 152 of second portion 150 may be aligned with agent inlet 118 so as to be in fluid communication with agent inlet 118. Therefore, agent 16 may be permitted to pass into opening 152, via agent inlet 118. Agent may be unable to pass between third and fourth seals 154, 156 and surface(s) 202, maintaining agent 16 in a desired location so that it will pass through opening 152.

Meanwhile, first portion 140 may remain in the same position or in approximately the same position as in the second configuration (FIG. 2B). Therefore, fluid from source 24 may continue to flow as described above, with respect to FIG. 2B. Second spring 168 and/or actuation mechanism 30 may be configured so that, after second spring 168 is compressed by a specified amount, neither of first portion 140 or second portion 150 may move further in the first direction, to maintain the third configuration of FIG. 2C. In the third configuration, second spring 168 may be fully compressed or may be only partially compressed.

After agent 16 passes through opening 152, agent 16 may pass through fourth opening 212, into mixing chamber 214.

There, agent 16 may combine with fluid from source 24. The combined agent 16 and fluid from fluid source 24 may then pass through outlet 134, to be delivered to a desired location.

After actuation mechanism 30 is no longer activated, a restoring force of second spring 168 may return valve 138 to the second configuration, in which fluid from source 24 is delivered, but agent 16 is not delivered. Then, a restoring force of first spring 162 may return valve 138 to the first configuration, in which neither of fluid from source 24 nor agent 16 is delivered.

It will be appreciated, although the above description describes the second configuration (FIG. 2B) as resulting from compression of first spring 162 without compression of second spring 168, that both first and second springs 162, 164 may be compressed in the second configuration so as to align seals 142, 144, 154, 156, 158 as described above to allow delivery of only fluid from source 24. Furthermore, in transitioning from the second configuration (FIG. 2B) to the third configuration (FIG. 2C), first spring 162 may experience further compression (first spring 162 may not be fully compressed in the second configuration).

Furthermore, it will be appreciated that there are numerous configurations of valve 138 in between the first and second configurations and in between the second and third configurations, For example, configurations may exist in which a portion of agent inlet 118 is covered and a portion of agent inlet 118 is aligned with opening 152 so that opening 152 is in fluid communication with agent inlet 118. In such a configuration, a relatively smaller amount of agent 16 may be permitted to pass through opening 152, compared with the third configuration (FIG. 2B). As valve 138 transitions between the second configuration (FIG. 2B) and the third configuration (FIG. 3B), an increasing amount of agent inlet 118 may align with opening 152, allowing an increasing amount of agent 16 to pass into opening 152.

Body 112 may facilitate delivery of fluid from source 24 that is free from or substantially free from agent 16 through outlet 134 before delivery of agent 16 and after delivery of agent 16. This delivery of fluid from source 24 that is free from or substantially free from agent 16 may flush system 10, reducing or eliminating clogging.

Figure 3A:
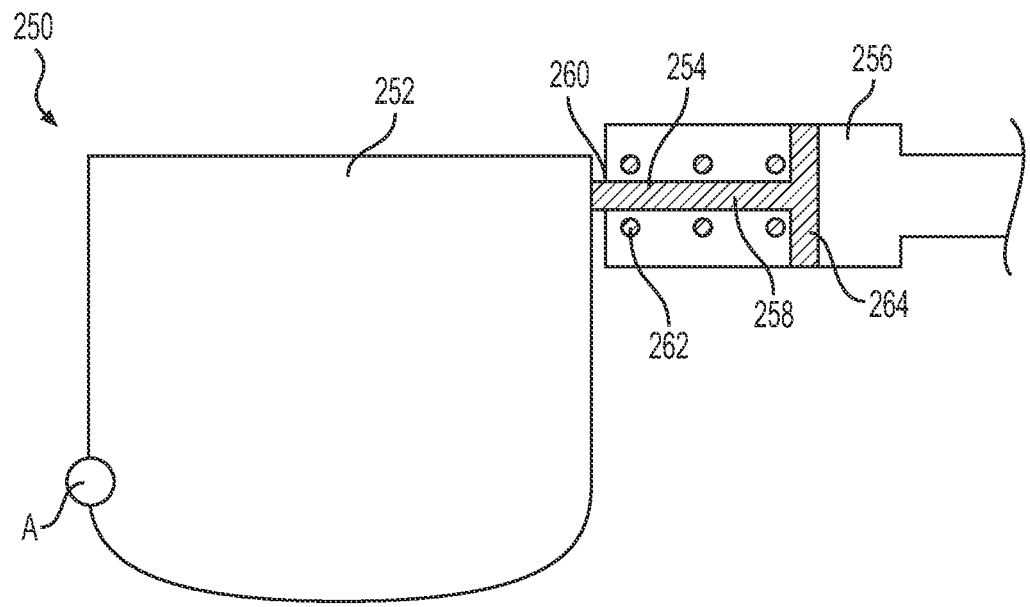
Figure 3B:
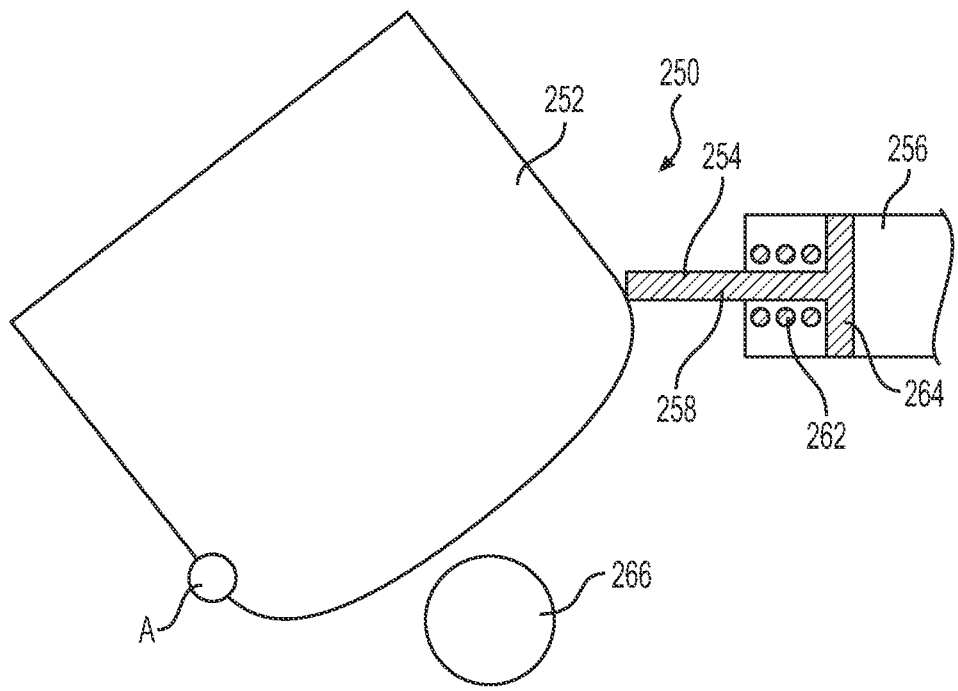

FIGS. 3A and 3B show an exemplary metering mechanism 250, which may be used as a portion of delivery system 10. FIGS. 3A and 3B both show views with enclosure 14 removed, looking in a direction toward agent inlet 18 and body 12 (i.e. enclosure 14 would be coming out of the top of the page of FIGS. 3A and 3B).

As shown in FIGS. 3A and 3B, metering mechanism 250 may include a door 252, which may pivot about a fixed pivot point A, and which may be a knife-edge door that has a very thin thickness in a direction parallel to a longitudinal axis of agent inlet 18. As shown in FIGS. 3A and 3B, door 252 may have a shape that includes any combination of straight and rounded sides. For example, door 252 may have three straight sides and one rounded side. Pivot point A may be located between one of the straight sides and the rounded side.

Metering mechanism 250 may also include a piston 254. Piston 254 may be disposed partially within a chamber 256, and a stem 258 of piston 254 may extend through an opening 260 in a wall of chamber 256. A spring 262 may also be disposed within chamber 256. Stem 258 of piston 254 may extend along a central axis of spring 258.

Chamber 256 may be fluidly connected to a source of fluid, such as source 24. When the fluid 24 enters chamber 256, chamber 256 may be pressurized, and the fluid may exert a force on a head 264 of piston 254, in a first direction toward opening 260. The force from the fluid may cause piston 254 to move in the first direction. A seal (not shown) may be disposed between chamber 256 and one or both of stem 258 and head 264, so that the fluid may not exit chamber 256. As piston 254 moves in the first direction (to the left in FIG. 3A), piston 254 may compress spring 262, generating a restorative force in a second direction, opposite the first direction. A movement of piston 254 in the first direction may stop when any of the following occurs (1) head 264 presses against surfaces of chamber 256; (2) a restorative force of spring 262 is equal to a force of the fluid on piston 254; and/or (c) spring 262 is fully compressed.

In a first configuration of metering mechanism 250, shown in FIG. 3A, spring 262 may be in a relaxed state (such as when no fluid is supplied to chamber 256). Door 252 may be in a first position. FIG. 3B shows a second configuration of metering mechanism 250, in which spring 262 is compressed, and piston 254 has moved in the first direction (due to fluid supplied to chamber 256). Door 252 may be in a second position.

When a user activates actuation mechanism 30, fluid (e.g., from source 24) may flow into chamber 256. Piston 254 and door 252 may be configured such that, when fluid is supplied to chamber 256, as piston 254 moves in the first direction, piston 254 exerts a force on door 252 in the first direction. The force of piston 254 may cause door 252 to rotate about pivot point A. As door 252 rotates, it may expose an opening 266, which may be in fluid communication with a chamber (not shown) of body 12. At first, after piston 254 begins moving in the first direction, only a portion of opening 266 may be exposed due to rotation of door 252. As piston 254 continues to move in the first direction, door 252 may continue to rotate, and more of opening 266 may be exposed. When piston 254 is fully extended (FIG. 3B), an entirety of opening 266 may be exposed. In the first position of door 252 (FIG. 3A), door 252 covers opening 266, so that opening 266 does not communicate with enclosure 14, and no agent 16 can pass into opening 266.

When actuation mechanism 30 is no longer activated, pressure may be released from chamber 256 (via, e.g., a release valve, which is not shown). Spring 262 may urge head 264 of piston 254 in the second direction, away from the opening 260, due to the restoring force of spring 262. Thus, piston 254 may no longer exert a force on door 252. The restoring force of spring 262 may cause piston 254 to return to the first configuration (FIG. 3A). Door 252 may also be biased to return to the first configuration (FIG. 3A). For example, door 252 may be spring biased at, e.g., at pivot point A.

In use, when actuation mechanism 30 is activated, such activation may cause fluid to pass through fluid inlet 20 and out of outlet 34. Meanwhile, as described above, actuation mechanism 30 may begin to expose opening 266. A portion of opening 266 may not immediately be exposed due to a delay in pressurizing chamber 256, or a delay in exposing opening 266 once chamber 256 is pressurized. Additionally or alternatively, a size of a portion of opening 266 that is exposed may initially be sized such that agent 16 does not flow through opening 260, or only a small amount of agent flows through opening 260. Thus, initially after actuation mechanism is activated, only fluid from source 24 may initially flow from outlet 34, without any agent 16.

Similarly, fluid may continue to be delivered via outlet 34, after actuation mechanism 30 begins or finishes transitioning from the second configuration (FIG. 3B) to the first configuration (FIG. 3A). For example, actuation mechanism 30 may be configured so that chamber 256 is depressurized before fluid stops passing through fluid inlet 20. Opening 266 may be covered partially or entirely by door 252, while fluid continues to pass through fluid inlet 20.

Metering mechanism 250 may facilitate delivery of fluid from source 24 that is free from or substantially free from agent 16 through outlet 34 before delivery of agent 16 and after delivery of agent 16. This delivery of fluid from source 24 that is free from or substantially free from agent 16 may flush system 10, reducing or eliminating clogging.

Figure 4A:
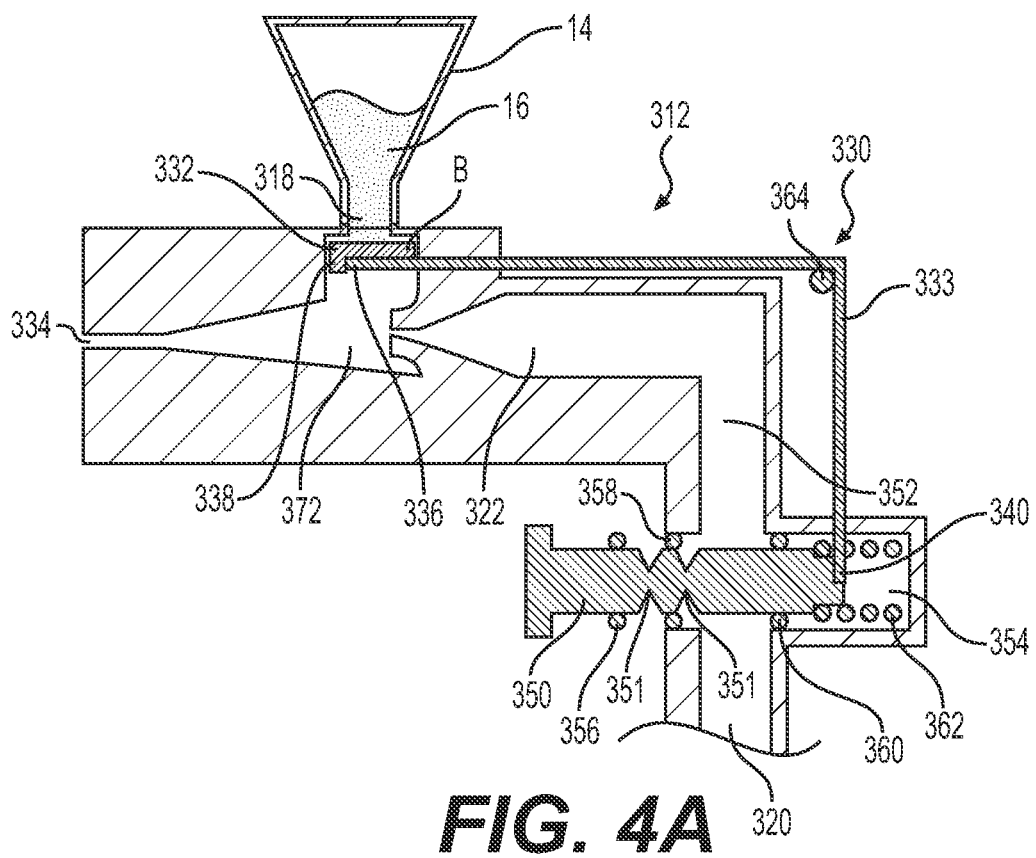
Figure 4B:
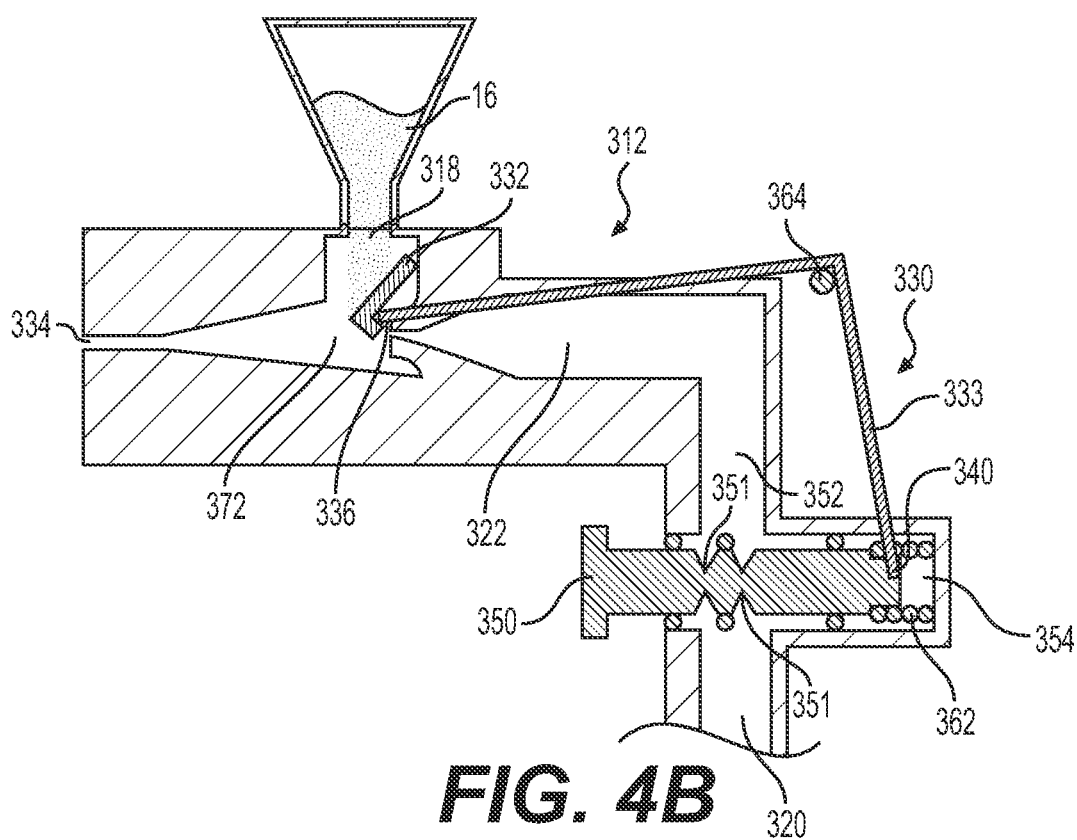

FIGS. 4A-4B show cross-sectional views of an exemplary body 312 for use with delivery system 10. Body 312 may include an agent inlet 318, which may be in fluid communication with enclosure 14 storing an agent 16. Body 312 also may include a fluid inlet 320 for receiving fluid from source 24 (see FIG. 1B). Body 312 may also include a metering mechanism 330 for controlling flow of fluid through fluid inlet 320 and agent 16 through agent inlet 318. Metering mechanism 330 may have any of the features of metering mechanism 250.

Metering mechanism 330 may include a door 332, which may have any of the properties of door 252. Door 332 may be configured to rotate about a hinge B. Door 332 may also be operatively connected to a wire 333. For example, a portion of door 332 that is on an opposite side of door 332 from hinge B may be operatively connected to wire 333. A first end 336 of wire 333 may be attached to a ridge 338 extending from an edge of door 332 in a direction parallel to a longitudinal axis of agent inlet 318.

A second end 340 of wire 333 may be operatively connected to a valve 350. Valve 350 may be operatively connected to an actuation mechanism 30 or may include a surface which serves as an actuation mechanism 30 by receiving contact from a finger of a user. Valve 350 may be received within a fluid channel 352, which may be in fluid connection with fluid inlet 320 and a fluid nozzle chamber 322. A longitudinal axis of valve 350 may be approximately perpendicular to a longitudinal axis of fluid channel 352. Valve 350 may also be received within a valve channel 354, which may have a longitudinal axis that is approximately parallel to a longitudinal axis of valve 350. Valve 350 may include first, second and third seals 356, 358, 360, which may be, for example, O-ring seals. Seals 356, 358, 360 may prevent air from entering valve channel 354 from fluid channel 352. Valve 350 may be dimensioned and formed of a material such that, in the configuration of FIG. 4A, valve 350 blocks fluid channel 352, such that fluid from fluid inlet 320 may not pass valve 350 to enter fluid nozzle chamber 322. For example, valve channel 354 may have a larger cross-sectional area than a cross-sectional area of fluid channel 352, and valve 350 may occupy an entirety or approximately an entirety of valve 354.

Door 332 may be biased such that, when no force is exerted on door 332 from wire 333 and door 332 is in a relaxed configuration, door 332 is approximately perpendicular or otherwise transverse to a central longitudinal axis of agent inlet 318, such that agent 16 may not pass door 332 to pass through fluid inlet 320. For example, door 332 may be spring-biased at pivot point B. FIG. 4A shows a first configuration of body 312, in which door 332 is in a relaxed configuration, effectively closing agent inlet 318 so that agent inlet 318 is not in communication with a mixing chamber 372.

Valve 350 may be movable in first and second directions, perpendicular to a longitudinal axis of fluid channel 352 and parallel to a longitudinal axis of valve channel 354. As valve 350 moves in the first direction, narrowed portions 351 of valve 350 may move such that they are disposed within fluid channel 352, and fluid may move past valve 350. The narrowed portions may have a cross-sectional area that is smaller than that of fluid channel 352, so that fluid may pass valve 350. Therefore, movement of valve 350 in the first direction may activate flow of fluid from fluid inlet 320 into fluid nozzle chamber 322.

Movement of valve 350 in the first direction may compress a spring 362. When spring 362 is in a neutral, relaxed configuration, door 332 may also in its relaxed configuration (the configuration to which door 332 is biased), so that agent 16 may not flow past door 332 into agent inlet 318.

As valve 350 moves in the first direction, valve 350 may move second end 340 of wire 333 in the first direction (to the right in FIGS. 4A-4B). As a result, first end 336 of wire 333 may move in the first direction. Alternatively, first end 336 of wire 333 may move in another direction such that a force from first end 336 of wire 333 causes door 332 to pivot about hinge B. Wire 333 may be routed over a pulley 364, to accommodate space for other components of body 312 and/or delivery system 10.

When first end 336 of wire 333 moves in the first direction, it may exert a force on ridge 338 in the first direction, which may cause door 332 to pivot such that an angle between door 332 and fluid inlet 320 increases (gets closer to 180 degrees) as door 332 pivots. As door 332 pivots, agent 16 may begin to flow past agent inlet 318 and door 332. Valve 350 and/or door 332 may stop moving when any one or more of the following occurs: door 332 contacts a surface defining agent inlet 318 or other structure of body 312, spring 362 reaches a maximum compression against a surface of valve channel 354, or a surface of valve 350 reaches a stop (not shown). FIG. 4B shows body 312 in a second configuration, in which door 332 is fully open.

Upon initial activation of actuation mechanism 30, door 332 may gradually pull away from agent inlet 318, yet fluid may flow through a fluid nozzle chamber 322, into a mixing chamber 372, and out of outlet 334, before any agent 16 or an appreciable amount of agent 16 is able to enter mixing chamber 372. Opening of door 332 may occur after valve 350 permits flow of fluid from fluid inlet 320. Once door 332 is opened a sufficient amount upon further activation of actuation mechanism 30, agent 16 may enter mixing chamber 372 to be mixed with fluid and to be delivered out of outlet 334. After actuation mechanism 30 is deactivated, door 332 may begin to return to its unbiased position. Closing of agent inlet 318 may allow a flow of fluid out of outlet 334 without any or an appreciable amount of agent 16 entering a mixing chamber 372. A flow of fluid without agent 16, or appreciable amounts of agent 16, before and after a flow of fluid combined with agent 16 may lessen clogging of portions of system 10.

Alternatively, other portions of body 312 may facilitate a flow of fluid without agent 16 before and after a flow of fluid combined with agent 16. For example, properties of spring 362 and/or slack in wire 333 may delay opening of door 332, and/or actuation mechanism 30 may be configured to permit a flow of fluid before movement of valve 350 in the first direction commences and after valve 350 returns to its unbiased configuration following delivery of agent 16 (FIG. 3A). Body 312 may facilitate delivery of fluid from source 24 that is free from or substantially free from agent 16 through outlet 334 before delivery of agent 16 and after delivery of agent 16. This delivery of fluid from source 24 that is free from or substantially free from agent 16 may flush system 10, reducing or eliminating clogging.

Figure 5A:
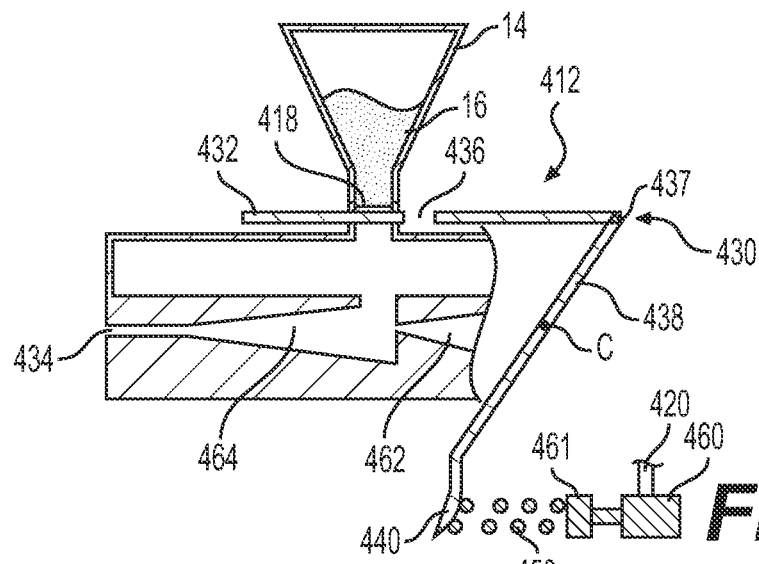
Figure 5B:
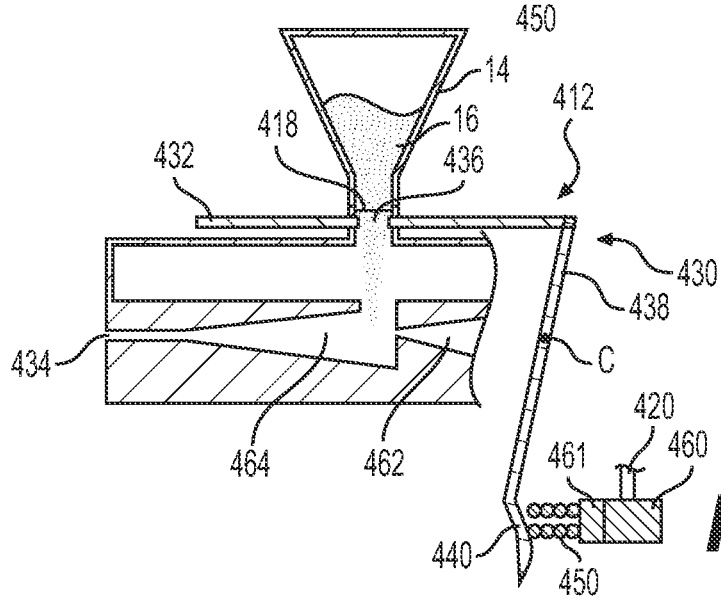

FIGS. 5A-5B show cross-sectional views of an exemplary body 412, which may be a portion of delivery system 10.

Body 412 may include a metering mechanism 430. Metering mechanism 430 may include a slider 432 (a first rigid member), which may be made from any suitable material (e.g., plastic, metal, composites, polymers, etc.) Slider 432 may be made of rigid or substantially rigid material. Slider 432 may include an opening 436 formed therein. Slider 432 may be configured to translate or slide in first and second directions relative to a remainder of body 412. A longitudinal axis of slider 432 may be transverse (e.g., perpendicular) to a longitudinal axis of an agent inlet 418, and movement of slider 432 may be axial along the longitudinal axis of slider 432.

Figure 5C:
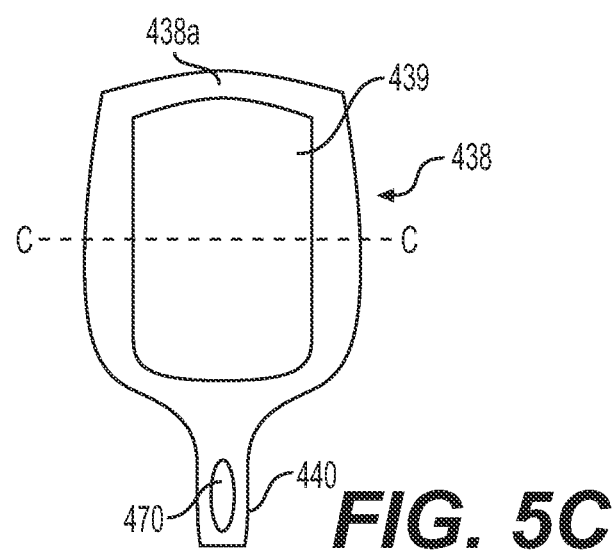

Slider 432 may be pivotably coupled to an arm 438 (a second rigid member) via, e.g., a hinge 437. Slider 432 may be received within a channel (not shown) or otherwise constrained so that slider 432 may only translate along the first and second directions (i.e., axial movement). Hinge 437 may be similarly translatable within that channel. Arm 438 may be rotatable about an axis C, extending into and out of the page as shown in FIGS. 5A and 5B. Axis C is also shown in FIG. 5C relative to arm 438. Arm 438 may include a trigger 440 at one end of arm 438. Trigger 440 may be contacted by a user in order to rotate arm 438 about axis C and thereby translate slider 432. Arm 438 may have an approximately rectangular shape, as shown in FIG. 5C. An opening 439 in arm 438 may receive components of body 412 (e.g., a fluid nozzle chamber 462). A top bar 438a of arm 438 may connect to slider 432 at hinge 437.

As trigger 440 is depressed, trigger 440 may compress a spring 450. Spring 450 may be operatively coupled to a button valve 460. Button valve 460 may be operative to allow and disallow flow from source 24 through a fluid inlet 420.

A first configuration of metering mechanism 430 is shown in FIG. 5A. In the configuration of FIG. 5A, spring 450 may be in a relaxed, uncompressed state that biases trigger 440 to the configuration of FIG. 5A. Opening 436 of slider 432 may be offset from agent inlet 418, such that agent 16 may not pass through opening 436 and agent inlet 418.

In use, an operator may depress trigger 440, which may be an example of actuation mechanism 30. A greater force may be required to compress spring 450 than to open button valve 460 to allow force of fluid from source 24 through fluid inlet 420. For example, a compression of trigger 440 required to depress a button 461 of button valve 460 and open button valve 460 may be approximately 0.075 inches. Additionally or alternatively, spring 450 may partially compress to open button valve 460, and further compression of spring 450 may be required in order to translate opening 436 sufficiently that it is in communication with agent inlet 418. A further compression of trigger 440 required to compress spring 450 may be approximately 0.33 inches. Thus, a total throw of trigger 404 may be approximately 0.504 inches. A force depressing trigger 440 may initially translate spring 450 to open button valve 460 and to activate flow of fluid from source 24 through fluid inlet 420. Fluid may flow into fluid inlet 420, into a fluid nozzle chamber 462. Fluid may pass through an opening 462 of fluid nozzle chamber 462, into mixing chamber 464. Fluid may then exit via outlet 34. In the first configuration, agent 16 may not be delivered via outlet 434, since opening 436 is not aligned with agent inlet 418.

Thereafter, as force on trigger 440 is increased, spring 450 may be compressed (or may be further compressed). Compression of spring 450 will enable arm 438 to rotate about axis C (or further about axis C). Rotation of arm 438 may, in turn, cause slider 432 to translate in the first direction (to the left in the Figures), aligning opening 436 with agent inlet 418, transitioning metering mechanism 430 to the second configuration of FIG. 5B. In the second configuration, fluid from source 24 may continue to flow as described above, with respect to the first configuration (FIG. 5A). Because opening 436 is aligned with agent inlet 418 and in fluid communication with agent inlet 418, agent 16 may also pass through opening 436 and agent inlet 418. Agent 16 may then enter mixing chamber 464, where it may mix with fluid from source 24. The combined agent 16 and fluid may then be delivered via outlet 434.

Trigger 440 may include an opening 470, which may be, for example, an elliptical shape. Opening 470 may receive components (not shown) that couple trigger 440 to spring 450, while allowing for necessary movement of trigger 440 relative to stationary spring 450 and button valve 460.

When a user releases trigger 440, spring 450 may first decompress, causing slider 432 to return to a configuration that misaligns opening 436 and agent inlet 418. Because opening 436 may be offset from agent inlet 418, agent 16 may not pass through agent inlet 418. However, because button valve 460 may remain open, fluid may continue to flow from source 24 through fluid inlet 20 for a time, until button valve 460 then closes.

Body 412 may facilitate delivery of fluid from source 24 that is free from or substantially free from agent 16 through outlet 434 before delivery of agent 16 and after delivery of agent 16. This delivery of fluid from source 24 that is free from or substantially free from agent 16 may flush system 10, reducing or eliminating clogging.

Figure 6A:
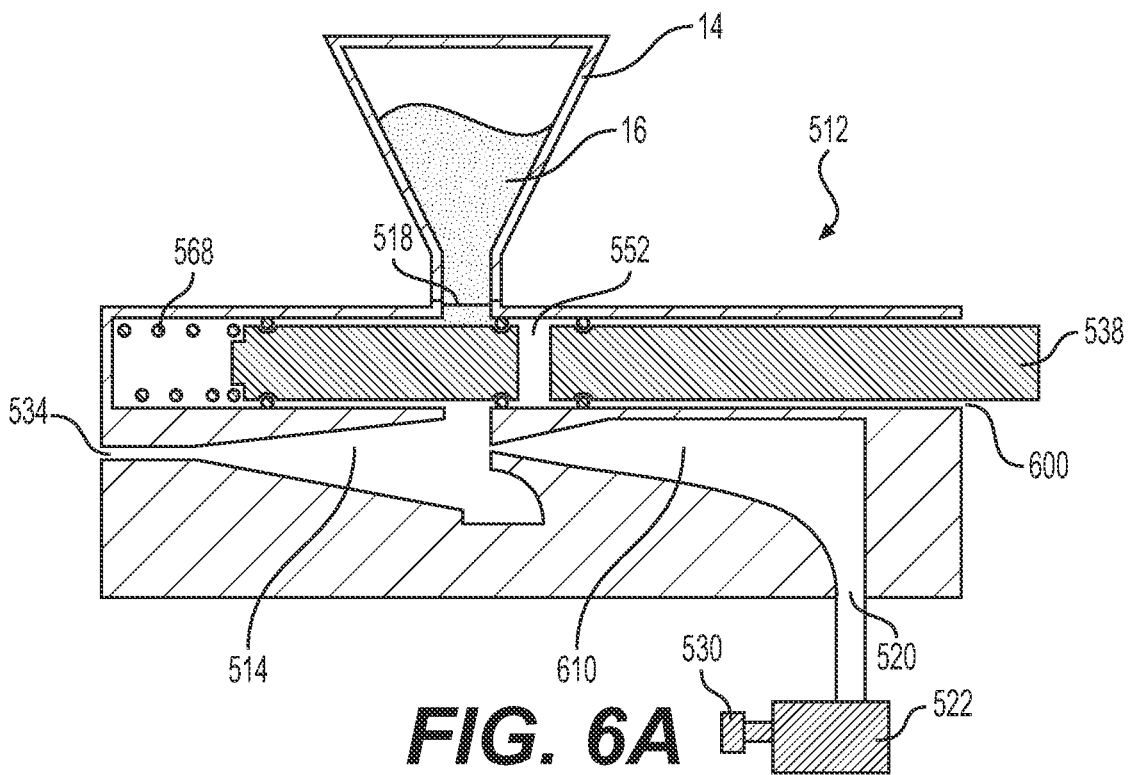
Figure 6B:
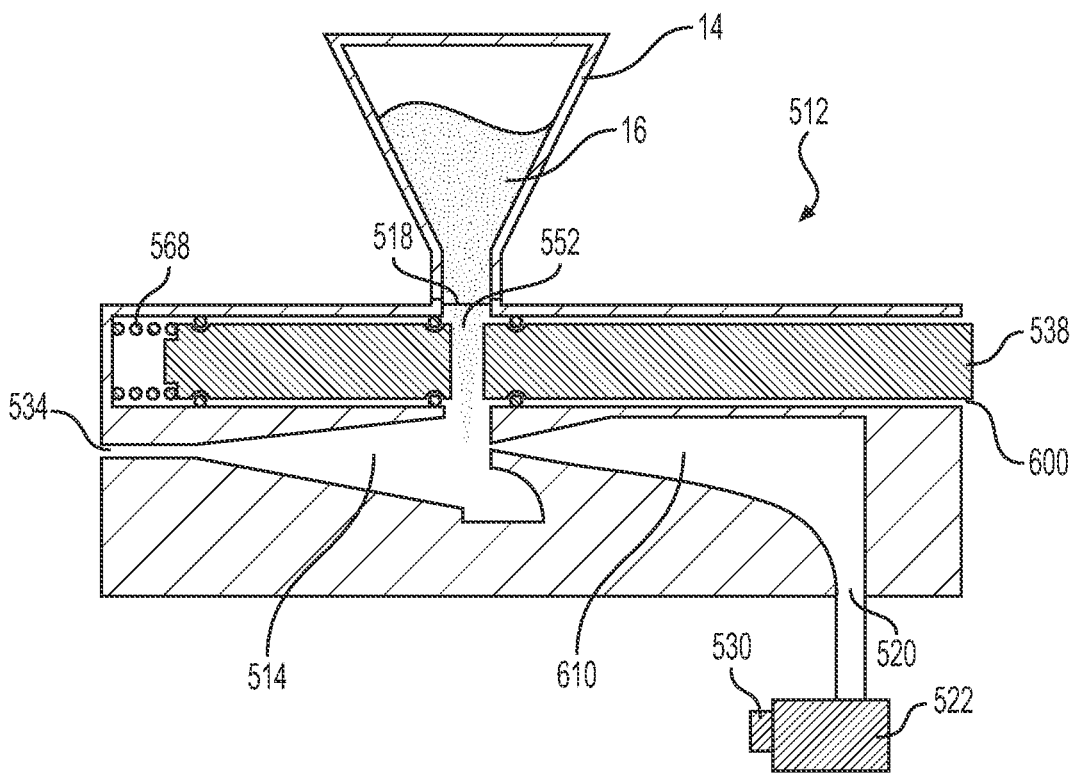

FIGS. 6A-6B show another example body 512, which may be a component of system 10. Body 512 may have any of the features of body 112 of FIGS. 2A-2C. The discussion of FIGS. 6A and 6B, herein, highlights differences between body 112 and body 512. A fluid inlet 520 of body 512 may be in direct fluid communication with a fluid nozzle chamber 610, without requiring fluid to first pass through a cavity 600. A valve 538 may include only one stem portion 550, which may have any of the properties of second portion 150. Stem portion 550 may include an opening 552 (like opening 152) and may be sealingly slidable within cavity 600.

Flow to fluid inlet 520 may be controlled via a valve 522, which may be, for example, a button valve. Valve 522 may actuate independently of valve 538. Thus, valve 522 may be opened, allowing a flow of fluid to enter fluid inlet 520 and exit outlet 534. Meanwhile, valve 538 may separately be actuated to permit flow of agent 16 through agent inlet 518.

FIG. 6A shows a first configuration, in which valve 522 is closed and valve 538 is in a first configuration, in which opening 552 is not aligned (not in fluid communication) with an agent inlet 518. In the first configuration, fluid may not pass through fluid inlet 20, and agent may not pass through agent inlet 518, so that neither fluid nor agent is delivered via outlet 534.

FIG. 6B shows a second configuration, in which valve 522 is open and valve 538 is in a second configuration, in which opening 552 is aligned with agent inlet 518 so as to be in fluid communication with agent inlet 518. In the second configuration, fluid may pass through fluid inlet 520, and agent 16 may pass through agent inlet 518, so that fluid and agent 16 may combine in mixing chamber 514 and be delivered from outlet 534.

Body 512 may be configured so that valve 538 may be actuated to the second configuration only when valve 522 is open. Thus, agent 16 may not enter mixing chamber 514 if fluid from source 24 is not also delivered to mixing chamber 514. In operation, a user may actuate a first actuation mechanism 530 (which may be, for example, a button of valve 522). Fluid may flow through body 512 and out of outlet 534. A user may then actuate a second actuation mechanism (not shown) to transition valve 538 to the second configuration to deliver a combination of agent 16 and fluid. A user may not be able to release first actuation mechanism 530 without first releasing the second actuation mechanism. After the second actuation mechanism is released, valve 538 may transition back to the first configuration of valve 538 due to a restorative force of a spring 568, which may have any of the properties of second spring 168. A user may then release first actuation mechanism 530 to close valve 522 and stop flow of fluid through fluid inlet 520.

Body 512 may facilitate delivery of fluid from source 24 that is free from or substantially free from agent 16 through outlet 534 before delivery of agent 16 and after delivery of agent 16. This delivery of fluid from source 24 that is free from or substantially free from agent 16 may flush system 10, reducing or eliminating clogging.

Figure 7A:
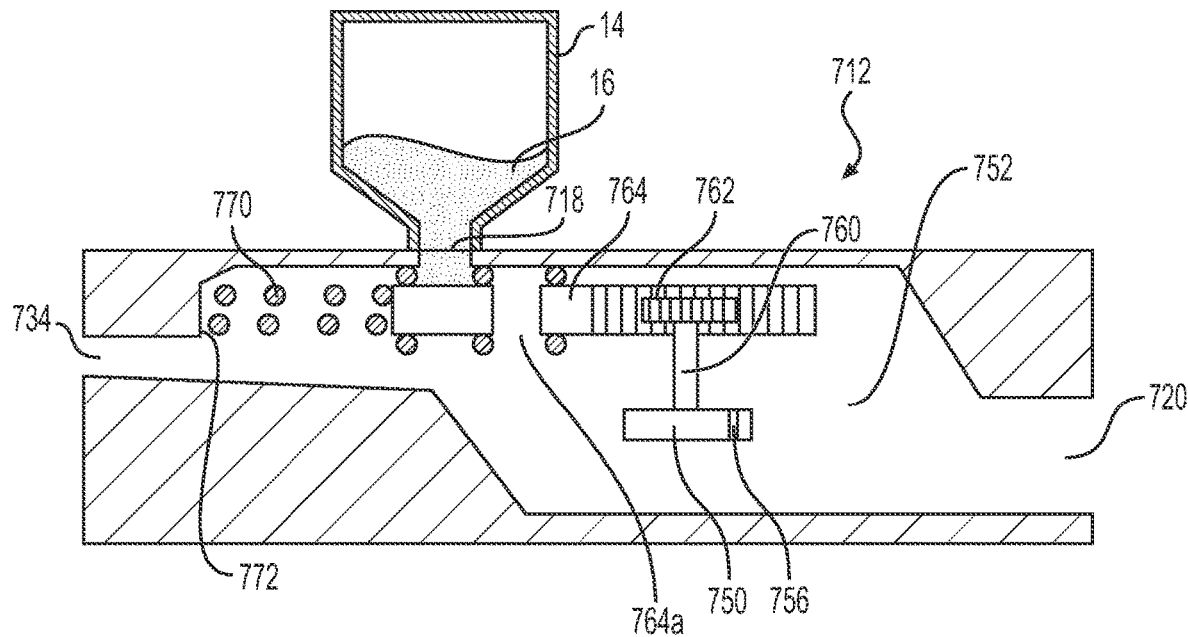
Figure 7B:
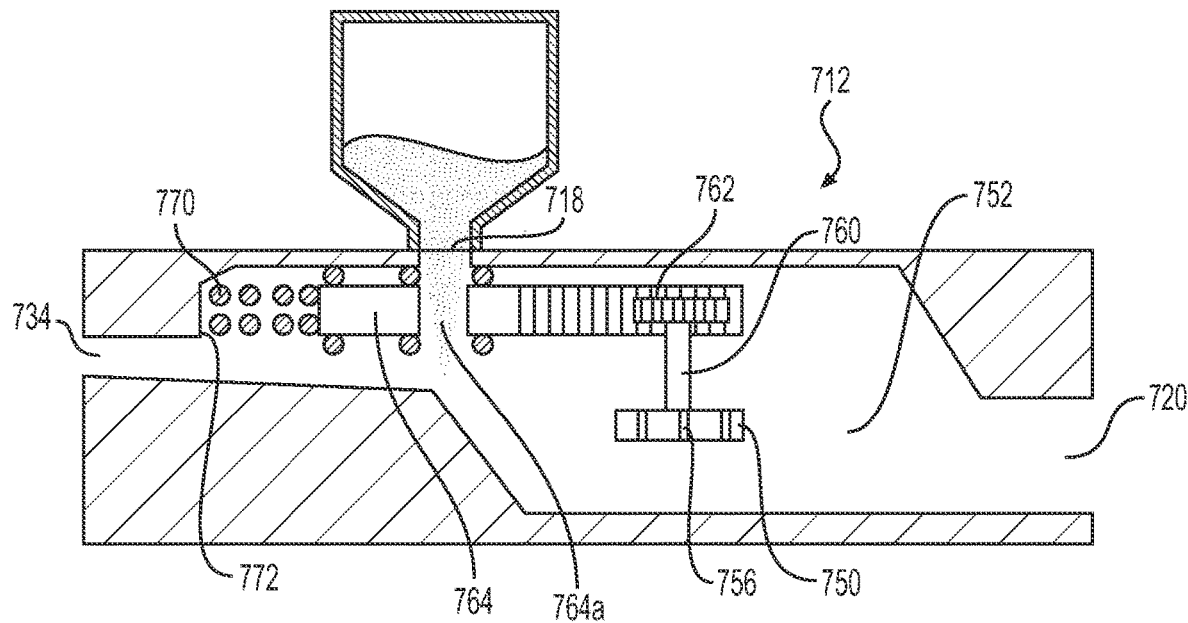
Figure 7C:
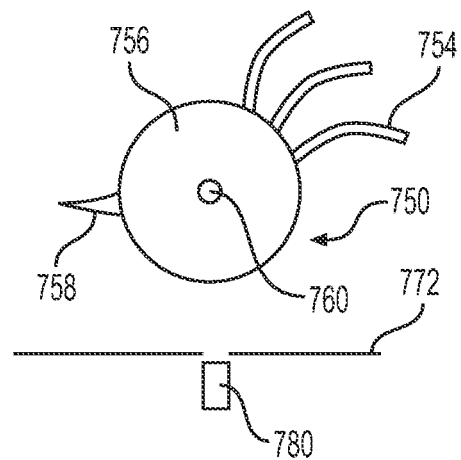
Figure 7D:
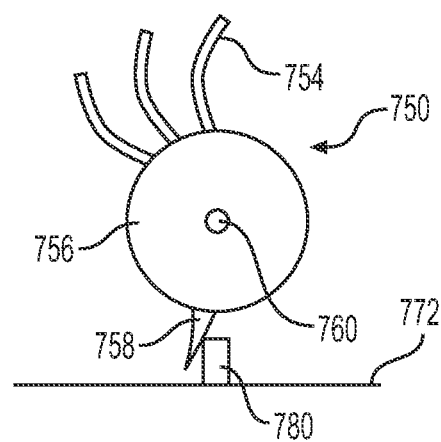

FIGS. 7A-7D show aspects of a body 712 that may form a part of delivery system 10. FIGS. 7A-7B show cross-sectional views of body 712 in first and second configurations, respectively, and FIGS. 7C-7D show aspects of a turbine 750 that may be a component of body 712.

As shown in FIGS. 7A and 7B, a body 712 may have an agent inlet 718, a fluid inlet 720, and an outlet 734, in fluid connection with one another via a chamber 752.

Turbine 750 may be disposed in chamber 752. Turbine 750 may include a plurality of blades 754 extending radially outward from a central body 756 (see FIGS. 7C-7D). Although three blades 754 are shown, it will be appreciated that other numbers of blades 754 may be utilized. Blades 754 may have any suitable shape, including the shape shown. Blades 754 may be formed from any suitable material, including rigid or flexible material, such as metals or plastics. Turbine 750 may also have a stop mechanism 758, which may extend radially outward from central body 756. Stop mechanism 758 may have any suitable shape, including a wedge shape, which may be a curved wedge shape. Stop mechanism 758 may be made from any suitable material, including rigid materials.

Turbine 750 may be fixedly connected to an axle 760 and may be rotatable about axle 760. Axle 760 may extend from central body 756 and may also be fixedly connected to a round gear 762, which may include teeth. Via axle 760, turbine 750 and gear 762 may rotate together, in unison. Gear 762 may be formed of any suitable material and may include any suitable number of teeth. Turbine 750 and gear 762 may have any suitable size.

Gear 762 may interact with a linear rack 764. Linear rack 764 may be movable relative to gear 762, along a direction transverse to a longitudinal axis of agent inlet 718 (e.g., perpendicular to agent inlet 718, left/right in the Figures). Rack 764 may include an opening 764a formed therein. A spring 770 may extend from an end of rack 764 furthest from gear 762, and a first end of spring 770 may be fixed relative to rack 764. A second end of spring 770 may be fixed relative to a surface 772 defining chamber 752.

In a first configuration, shown in FIG. 7A, actuation mechanism 30 (FIG. 1) may not be activated, and fluid may not flow from source 24 to fluid inlet 720. Turbine 750, gear 762, and rack 764 may each be stationary. Spring 770 may be in a relaxed state. Rack 764 may be positioned so that opening 764a is not aligned with (not in fluid communication with) agent inlet 718. Rack 764 may include seals 765 to prevent agent from moving between an outer surface of rack 764 and a surface of chamber 752. In the first configuration, agent 16 may not enter chamber 752 because opening 764a is not aligned with (not in fluid communication with) agent inlet 718.

When an actuation mechanism (FIG. 1) is activated, flow from source 24 to fluid inlet 720 may be permitted. Fluid from fluid inlet 720 may interact with blades 754 to cause turbine 750 to rotate. Rotation of turbine 750 may cause corresponding rotation of gear 762. Rotation of gear 762 may cause rack 764 to translate in a first direction (to the left in the Figures), such that opening 764a moves closer to agent inlet 718. Spring 770 may be compressed as rack 764 translates, because a force from fluid on turbine 750 may overcome a restorative force of spring 770. As shown in FIG. 7B, in a second configuration of body 712, opening 764a may be aligned with (in fluid communication with) agent inlet 718. Thus, agent 16 may be permitted to flow through opening 764a and into chamber 752. In chamber 752, agent 16 may mix with the fluid from source 24 and then exit through outlet 734. However, before opening 764a is aligned with (in fluid communication with) agent inlet 718, only fluid from source 24 may flow through chamber 752 and exit outlet 734.

Activation of actuation mechanism 30 may cause, either immediately or following a delay, a tab 780 to extend from a surface 772 of body 712. Tab 780 may extend in a direction perpendicular to axle 760. FIG. 7C shows turbine 750 and tab 780 prior to extension of tab 780 (e.g., prior to activation of actuation mechanism 30). FIG. 7D shows turbine 750 and tab 780 after tab 780 has been extended from surface 772. Tab 780 may interact with stop mechanism 758 to prevent further rotation of turbine 750 after stop mechanism 758 contacts tab 780. Tab 780 and stop mechanism 758 may stop gear 762 from continuing to rotate and thereby stop rack 764 from translating past a desired position, where opening 764a aligns with agent inlet 718.

When actuation mechanism 30 is released, a flow of fluid through fluid inlet 720 may be eliminated or reduced, thereby eliminating or reducing a force on blades 754. A restorative force of spring 770 may overcome a force of fluid (if any) on turbine 750, causing rack 764 to translate in a second direction, opposite the first direction. Rack 764 may, in turn, cause rotation of gear 762, which may cause rotation of turbine 750, in a direction opposite to a direction of rotation while translating from the first configuration to the second configuration. Tab 780 may also retract. Opening 764a may no longer be aligned with (in fluid communication with) agent inlet 718, so agent 16 may no longer flow through agent inlet 718. Where some flow of fluid through fluid inlet 720 continues, fluid may continue to exit outlet 734, after a flow of agent 16 has ceased. Alternatively, body 712 may include a purge line, which requires actuation by another mechanism (e.g., a button). Alternatively, actuation mechanism 30 may have three positions. In a first position of actuation mechanism 30, no flow of fluid through fluid inlet 720 may occur. In a second position, fluid may be permitted to flow, but tab 780 or another component may interact with rack 764 to stop movement of rack 764 before opening 764a aligns with agent inlet 718, thereby preventing flow of agent 16. In a second position, tab 780 or another component may be retracted/deactivated to permit rotation of turbine 750 and permit flow of agent 16 while fluid flows through fluid inlet 720. Alternatively, gear ratios between gear 762 and linear rack 764, a length of rack 764, and a strength of spring 770 may be chosen such that, when actuation mechanism 30 is activated, a known duration and/or amount of fluid from fluid inlet 720 may flow prior to alignment of opening 764a and agent inlet 718, providing a flow of fluid without agent 16. Following alignment of opening 764a and agent inlet 718, agent 16 may flow via agent inlet 718. If a user desires flow of fluid following a delivery of agent 16, the user may release actuation mechanism 30 and reactivate actuation mechanism 30. The user may only activate actuation mechanism for an amount of time such that fluid flows but agent does not flow (because opening 764a and agent inlet 718 do not align).

Body 712 may facilitate delivery of fluid from source 24 through outlet 734 before delivery of agent 16 and after delivery of agent 16. This delivery of fluid from source 24 may flush system 10, reducing or eliminating clogging.

While principles of the disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A device for delivering an agent, comprising:
a source of the agent;
a mixing chamber for receiving fluid and the agent;
a valve moveable relative to the mixing chamber and positioned downstream from the source of the agent;
an outlet in fluid communication with the mixing chamber to deliver the fluid and the agent; and
an actuator configured to move the valve relative to the mixing chamber to:
(1) a first configuration that blocks the agent from entering the valve and allows the fluid to move past the valve to deliver a first flow of the fluid substantially free from the agent through the outlet;
(2) a second configuration, after delivering the first flow, that simultaneously aligns an opening of the valve with an inlet of the source of the agent to receive the agent through the opening of the valve and allows the fluid to move past the valve to deliver a second flow of the fluid and the agent through the outlet; and
(3) a third configuration, after delivering the second flow, that blocks the agent from entering the valve and allows the fluid to move past the valve to deliver a third flow of the fluid substantially free from the agent through the outlet.

2. The device of claim 1, wherein the actuator transitions the valve from the first configuration to the second configuration, wherein, in the first configuration, the valve is positioned such that the source of the agent is not in fluid communication with the mixing chamber, and, wherein, in the second configuration, the valve is positioned such that the source of the agent is in fluid communication with the mixing chamber.

3. The device of claim 2, wherein, in the first configuration, the opening is not in fluid communication with the source of the agent and wherein, in the second configuration, the opening is in fluid communication with the source of the agent.

4. The device of claim 3, wherein the valve is able to transition from the first configuration to the second configuration only when a flow of the fluid is flowing through the mixing chamber, such that the valve is inhibited from moving from the first configuration towards the second configuration when the fluid is not flowing through the mixing chamber.

5. The device of claim 4, wherein the valve includes:
a first portion;
a second portion defining an opening; and
a spring extending from the first portion to the second portion, wherein, in the first configuration and a third configuration, the opening is not in fluid communication with the inlet of the source of the agent and wherein, in the second configuration, the opening is in fluid communication with the inlet of the source of the agent.

6. The device of claim 4, wherein the agent includes a powder, wherein, in the first configuration and a third configuration, the opening is not in fluid communication with the inlet of the source of the agent and wherein, in the second configuration, the opening is in fluid communication with the inlet of the source of the agent such that the powder can pass through the opening.

7. The device of claim 2, wherein the valve includes a first portion and a second portion, and wherein a spring connects the first portion to the second portion.

8. The device of claim 1, wherein the actuator includes a first actuator for controlling a flow of the agent from the source of the agent and a second actuator for controlling a flow of the fluid, wherein the first actuator and the second actuator are configured to be independently activated.

9. The device of claim 8, wherein the first actuator may be activated only if the second actuator is activated.

10. A device for delivering an agent, comprising:
a source of fluid;
a source of the agent;
a valve for selectively receiving the fluid and the agent;
a mixing chamber for receiving the fluid and the agent from the valve based on a position of the valve relative to the mixing chamber; and
an actuator configured to transition the valve from a first configuration to a second configuration, wherein, in the first configuration, the valve is positioned relative to the mixing chamber to block the agent from entering the valve such that the source of the agent is not in fluid communication with the mixing chamber and allow the fluid to move past the valve such that a first flow of fluid substantially free from the agent is received in the mixing chamber via the valve, and
wherein, in the second configuration, the valve is positioned relative to the mixing chamber to allow the agent to enter the valve such that the source of the agent is in fluid communication with the mixing chamber through the valve and simultaneously allow the fluid to move past the valve such that the agent and a second flow of fluid are received in the mixing chamber via the valve.

11. The device of claim 10, wherein the actuator is further configured to transition the valve from the second configuration to the first configuration after transitioning the valve from the first configuration to the second configuration.

12. A device for delivering an agent, comprising:
a source of the agent;
a source of a pressurized fluid;
a valve positioned downstream from the source of the agent and upstream from the source of the pressurized fluid, the valve including an opening; and
a mixing chamber for receiving the pressurized fluid and the agent via the valve;
wherein the valve is configured to move to a first position relative to the mixing chamber to fluidly decouple the opening from the source of the agent such that only the pressurized fluid is delivered to the mixing chamber via the valve, and a second position relative to the mixing chamber to fluidly couple the opening with the source of the agent such that the pressurized fluid and the agent are delivered to the mixing chamber via the valve.

13. The device of claim 12, wherein, in the first position of the valve, the source of the agent is not in fluid communication with the mixing chamber via the valve.

14. The device of claim 12, wherein, in the first position of the valve, the opening is offset from the source of the agent such that the agent is inhibited from entering the valve via the opening.

15. The device of claim 12, wherein, in the second position of the valve, the source of the agent is in fluid communication with the mixing chamber via the valve.

16. The device of claim 12, wherein, in the second position of the valve, the opening is aligned with the source of the agent such that the agent is permitted to enter the valve via the opening.

17. The device of claim 12, wherein, in the first position and the second position of the valve, the source of the pressurized fluid is in fluid communication with the mixing chamber via the valve.

18. The device of claim 17, wherein, in a third position of the valve, the source of the pressurized fluid is not in fluid communication with the mixing chamber via the valve.

19. The device of claim 18, wherein, in the third position of the valve, the source of the agent is not in fluid communication with the mixing chamber via the valve.

20. The device of claim 12, wherein the valve includes a cavity that is transverse to the opening for receiving the fluid from the source of the pressurized fluid.

* * * * *